US009943245B2

(12) United States Patent
Gu et al.

(10) Patent No.: US 9,943,245 B2
(45) Date of Patent: Apr. 17, 2018

(54) METHODS FOR MEASURING TISSUE IMPEDANCE AND DEVICES THEREOF

(71) Applicant: RetroVascular, Inc., Pleasanton, CA (US)

(72) Inventors: Xiang Ian Gu, Foster City, CA (US); Paul J. Lingane, Palomar Park, CA (US); Wayne Ogata, San Ramon, CA (US); Steven Meyer, Oakland, CA (US); Alireza Yavari, Sunnyvale, CA (US)

(73) Assignee: Retrovascular, Inc., Pleasanton, CA (US)

( * ) Notice: Subject to any disclaimer, the term of this patent is extended or adjusted under 35 U.S.C. 154(b) by 151 days.

(21) Appl. No.: 14/216,824

(22) Filed: Mar. 17, 2014

(65) Prior Publication Data

US 2014/0275912 A1 Sep. 18, 2014

Related U.S. Application Data (60) Provisional application No. 61/800,519, filed on Mar. 15, 2013.

(51) Int. Cl.
*A61B 5/053* (2006.01)
*A61B 5/00* (2006.01)

(52) U.S. Cl.
CPC .......... *A61B 5/0538* (2013.01); *A61B 5/6851* (2013.01); *A61B 5/7217* (2013.01)

(58) Field of Classification Search
CPC ..... A61B 5/053; A61B 5/0538; A61B 5/6851; A61B 5/6852–5/6859

(Continued)

(56) References Cited

U.S. PATENT DOCUMENTS

| 4,729,385 A | 3/1988 | Juncosa et al. |
| 2004/0082850 A1* | 4/2004 | Bonner ................ A61B 5/06 600/424 |

(Continued)

FOREIGN PATENT DOCUMENTS

| EP | 1 238 630 | 9/2002 |
| JP | 63194640 | 8/1988 |

(Continued)

OTHER PUBLICATIONS

International Preliminary Report on Patentability, corresponding to PCT/US2014/030720, dated Sep. 24, 2015.

(Continued)

*Primary Examiner* — Adam J Eiseman
(74) *Attorney, Agent, or Firm* — LeClairRyan, a Professional Corporation (57) ABSTRACT

A method and apparatus for measuring an impedance of a tissue region inside a body of a patient. A first guidewire is advanced into a tissue region of a body of a patient, wherein the first guidewire comprises one or more electrodes electrically coupled to the tissue region. A second guidewire is advanced into the body, wherein the second guidewire comprises one or more electrodes electrically coupled to the tissue region of the body of the patient and spaced from the first guidewire. An error correction electrode is electrically coupled to the body. A voltage is applied across the first and the second guidewires. The impedance of the tissue region between the first and the second guidewires is measured while using an electrical pathway created by the error correction electrode.

12 Claims, 4 Drawing Sheets

(58) Field of Classification Search
USPC .................................................. 600/547, 585
See application file for complete search history.

(56) References Cited

U.S. PATENT DOCUMENTS

| | | |
|---|---|---|
| 2004/0082962 A1 | 4/2004 | Demarais et al. |
| 2009/0131925 A1 | 5/2009 | Tempel et al. |
| 2010/0114231 A1 | 5/2010 | Kroll |
| 2011/0152712 A1* | 6/2011 | Cao .................... A61B 5/02007 600/547 |
| 2012/0016253 A1 | 1/2012 | Koh et al. |
| 2012/0053470 A1 | 3/2012 | Wong et al. |

FOREIGN PATENT DOCUMENTS

| | | |
|---|---|---|
| JP | 2004500171 | 1/2004 |
| JP | 4590027 | 9/2010 |
| JP | 2010540198 | 12/2010 |

OTHER PUBLICATIONS

International Search Report, corresponding to PCT/US2014/030720, dated Sep. 5, 2014.
European Search Report for corresponding EP Application No. 14762899.4, dated Aug. 9, 2016, pp. 1-9.
China Office Action for corresponding China Application No. 201480012890.6, dated Apr. 1, 2017.
Decision to Grant for JP Application No. 2016-503451, dated Feb. 19, 2018.

* cited by examiner

METHODS FOR MEASURING TISSUE IMPEDANCE AND DEVICES THEREOF

This application claims the benefit of U.S. Provisional Patent Application Ser. No. 61/800,519, filed Mar. 15, 2013, which is hereby incorporated by reference in its entirety.

FIELD

This technology relates to obtaining an in vivo impedance measurement for a target tissue region, and in particular, methods and devices for obtaining an in vivo impedance measurement that reduces measurement errors related to shunt capacitance.

BACKGROUND

Precise in vivo impedance measurement of biological tissues allows for accurate evaluation of the physiological condition of the tissue and proper implementation of medical treatment. Elimination of errors caused by the measuring tool itself is critical to improved measurement accuracy and enhanced treatment effect.

Conventional impedance measurement methods for biological tissues suffer from the inability to differentiate the true impedance value from the errors induced by the measuring tool itself. It is difficult to eliminate such errors since they are inherent to the measurement method and are embedded in the measured signal from the measuring tool.

Figure 1:
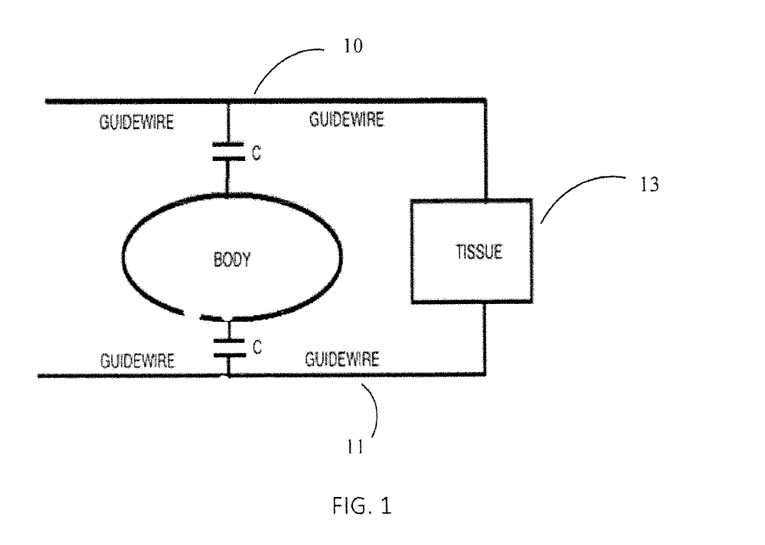
FIG. 1 is a partial block diagram and partial circuit diagram of a tissue impedance measurement system which demonstrates a measurement error that may be introduced.
Figure 2:
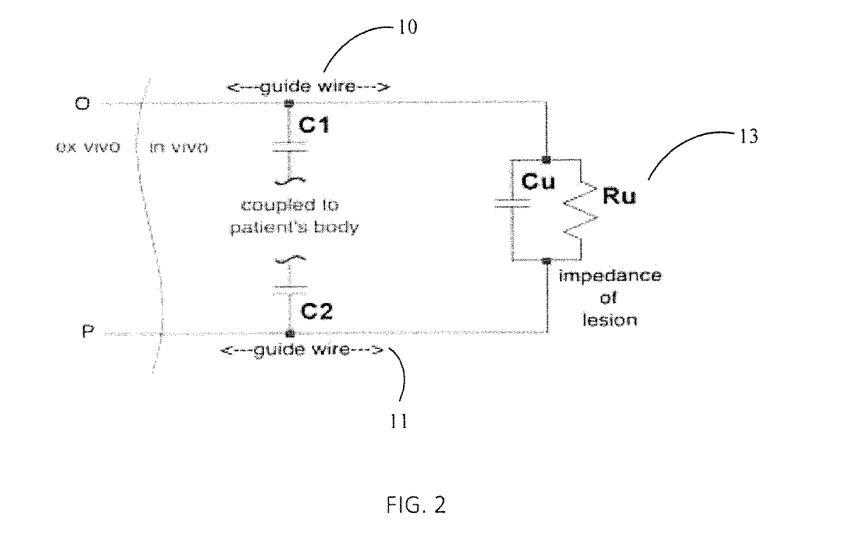
FIG. 2 is a circuit diagram of the tissue impedance measurement system illustrated in FIG. 1.

Referring to FIGS. 1 and 2, a measurement apparatus for measuring tissue impedance which demonstrates errors introduced into the measurement is shown. As seen in FIG. 1, two guidewires 10 and 11 are placed at or near a target tissue region 13 by traversing through body vessels. The impedance of the tissue region 13 (modeled as a capacitor and a resistor in parallel, Cu and Ru of FIG. 2, but could be any complex impedance) is of interest. The measurement may be made by a measuring device (not shown) connected to the proximal ends of each of the guidewires. Measurement error, however, may be created by measurement current flowing through the large capacitance to the body (the capacitance is modeled as capacitors C1 and C2, but is in fact distributed along the length of the guidewire). Capacitors C1 and C2 can be considered to be effectively in series with the patient's body, and will shunt away the current flowing through the tissue region 13 in parallel to C1 and C2, causing the measurement result to deviate from the true impedance values.

The measurement error can include, but is not limited to, common mode impedances, such as the shunt capacitance between the guidewires 10 and 11. Furthermore, the degree of measurement error may be influenced by certain conditions such as the electrical properties of the guidewires, especially the dielectric property of the shielding material of the two guidewires, the coating length and/or thickness of the shielding material of the two guidewires, the medium between the guidewires such, as tissue, fluid, and blood, or the driving signal.

Although methods have been developed to address certain measuring tool-induced errors, e.g., by making two impedance measurements to identify a true impedance value for the target tissue, limitations remain.

SUMMARY

A method for measuring an impedance includes advancing a first guidewire into a tissue region of a body of a patient, wherein the first guidewire comprises one or more electrodes electrically coupled to the tissue region. A second guidewire is advanced into the body, wherein the second guidewire comprises one or more electrodes electrically coupled to the tissue region of the body of the patient and spaced from the first guidewire. An error correction electrode is electrically coupled to the body. A voltage is applied across the first and the second guidewires. The impedance of the tissue region between the first and the second guidewires is measured while using an electrical pathway created by the error correction electrode.

An apparatus for measuring an impedance of a tissue region inside a body of a patient includes an energy source. A first guidewire and a second guidewire are coupled to the energy source. The first and second guidewires are configured to be advanced into a tissue region of a body of a patient. The first and second guidewires include one or more electrodes configured to be electrically coupled to the tissue region. An error correction electrode is configured to be in electrical connection with the body. A measurement device is configured to measure the impedance of the tissue region between the first and the second guidewires when a voltage is applied between the first and second guidewires while using an electrical pathway created by the error correction electrode.

This technology provides a number of advantages including providing methods and devices for measuring in vivo tissue impedance that reduce errors associated with shunt capacitance to provide for more accurate measurement of tissue impedance. In one aspect, this technology provides methods and devices for obtaining accurate measurement of target tissue impedance in vivo by using a third-terminal connection from a measuring device. This technology also improves the accuracy of in vivo impedance measurements of biological tissues, which may improve the accuracy of evaluations of the physiological condition of the tissue and proper implementation of medical treatment. Further, this technology is configured to reduce or eliminate errors affecting in vivo impedance measurements, which may improve treatment evaluation and improve the selection of treatment parameters and proper implementation of medical treatment.

Aspects of this technology also provide methods and devices for obtaining accurate measurement of target tissue impedance in vivo. In one example, this technology provides methods and devices for obtaining accurate measurement of target tissue impedance using a third-terminal connection from a measuring device. This technology also provides accurate in vivo impedance determinations in a single measurement. In addition, instead of addressing the inherent shunt capacitance caused by the measuring device itself (such as one or more measuring electrodes), this technology is configured to eliminate, reduce, mitigate, or correct the effect of the shunt capacitance induced between the measuring device and the patient's body, e.g., the capacitance from one electrode to the patient's body, and another capacitance from the other electrode to the patient's body.

DETAILED DESCRIPTION

Figure 3:
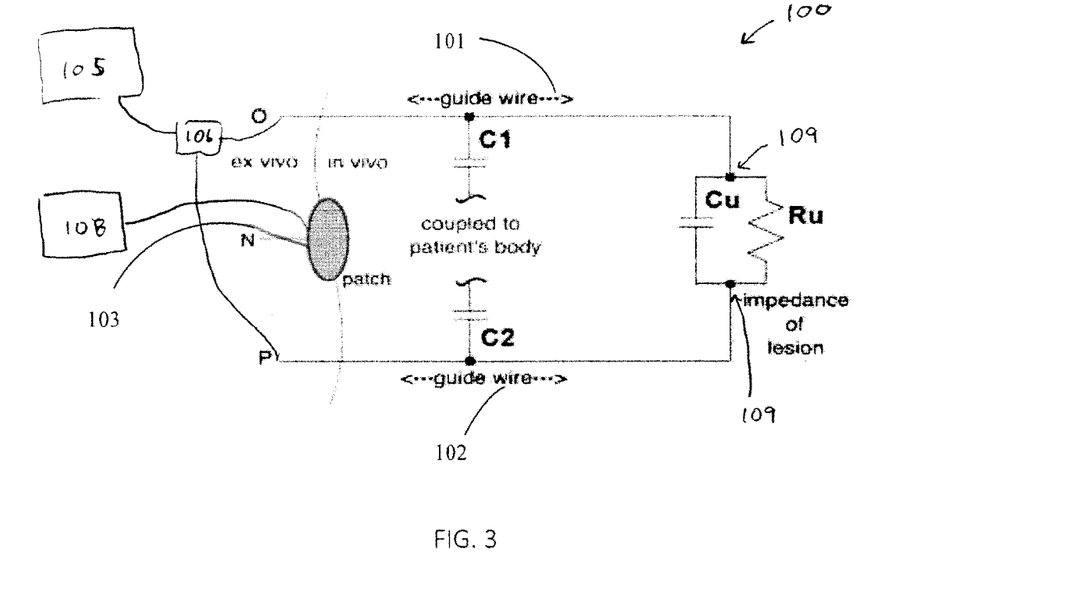
FIG. 3 is a partial block diagram and partial circuit diagram of an example of an apparatus for measuring in vivo tissue impedance while reducing error from shunt capacitance.

An example of an impedance measurement apparatus 100 is illustrated in FIG. 3. In this example, the impedance measurement apparatus 100 includes a first guidewire 101, a second guidewire 102, error correction electrode 103, energy source 105, and measurement device 108, although apparatus 100 can include other types and numbers of devices, components, and/or elements in a variety of other configurations. While not shown, the apparatus 100 also may include additional components which are well known to those skilled in the art and thus will not be described here. This technology provides a number of advantages including providing methods and devices for measuring tissue impedance while reducing errors in the measurement resulting from shunt capacitance as illustrated and described with reference to the examples herein.

Referring more specifically to FIG. 3, the apparatus 100 includes the first and second guidewires 101 and 102, which are independent guidewires, although apparatus 100 may include other types and/or numbers of guidewires. First and second guidewires 101 and 102 include electrodes 109 disposed at or near their distal ends, although the first and second guidewires 101 and 102 may include other types and/or numbers of electrodes or other conductors in other locations along the guidewires 101 and 102 such as, by way of example only, a plurality of electrodes arranged in an array. The first and second guidewires 101 and 102 may be, by way of example only, catheters, microcatheters, dilating catheters, or probes, although any other types of longitudinal members that can be inserted into the body. In one example, the exterior of the guidewires are covered by non-conductive layers which shield the guidewires electrically, thermally, chemically, and/or mechanically. In one example, the non-conductive layers comprise a sheath or a coating. Examples of such coating materials may include Teflon, ceramic, polyimide, parylene, or other suitable materials. Examples of methods which could be employed for coating may include standard or heat-shrink tubing, spraying, dipping, vapor deposition, or plasma deposition.

The first and second guidewires 101 and 102 are capable of being steered independently of the other to offer the operator the freedom to choose the optimal measurement location when advancing the first and second guidewires 101 and 102 in the body of the patient. Additionally, by using guidewires that are capable of being steered independently to measure impedance, the shunt capacitance created by the measurement device 108 can be reduced since the electrode wires do not have to be bundled together into a cable over an extended length.

The term "shunt capacitance" is used herein to mean the undesirable capacitance between the electrodes, guidewires or other devices and the patient's body that affects the impedance measurement across a target tissue region. Furthermore, "shunt capacitance" is used herein to mean any measurable stray capacitance in the tissue region such as stray capacitance due to any body tissue including blood in vessels or other fluids found in the body. In more general terms, "shunt capacitance" can be referred to as an exemplary indicator of any possible measurable resistive and reactive (capacitive or inductive) components from the measurement equipment that may contribute to the impedance measurement other than the tissue region between the measuring electrodes.

Additionally, in this example the first and second guidewires 101 and 102 are configured to be connectable to an energy source 105, such as a radio frequency (RF) generator, through a coupler 106, although other energy sources may be utilized. Conductive wires (not shown) connect the electrodes 109 of the first and second guidewires 101 and 102 to the coupler 106 to deliver energy from the energy source 105, such as an RF generator by way of example only, to the electrodes 109. The coupler 106 is configured to transmit the signals of the energy source 105 to the first and second guidewires guidewires 101 and 102.

Referring to FIG. 3, the error correction electrode 103 (also referred to herein as the third terminal) is shown as an ex vivo patch which is located on the body of the patient near the tissue region to be measured, although the error correction electrode 103 may have various other configurations and shapes. Furthermore, the error correction electrode 103 may be located on a device, such as a guidewire wire by way of example only, that can be inserted into the body and be used in vivo. Various direct connections or other connection options to implement the error correction electrode 103 and the resulting error correction pathways are contemplated in light of specific situations.

The error correction electrode 103 is configured to be connectable to a measurement device 108 which include measurement circuitry (not shown) and is used to reduce the effect of the shunt capacitance caused by the first or the second guidewires 101 and 102 by using a third-terminal path that is created by the connection from the error correction electrode 103 attached to the patient's body. In one example, the third-terminal path is created by a connection between the error correction electrode 103 or equivalent from the impedance measurement circuitry and the vessel blood sharing the same path with the first and second guidewires 101 and 102 which induces the shunt capacitance. In one example, the establishment of the third-terminal path will enable the automatic cancellation of error and allows for accurate measurement of Cu and Ru even in the presence of capacitances C1 and C2.

In one exemplary operation of the example shown in FIG. 3, the first guidewire 101 is first advanced into a body of a patient. Contemporaneously or sequentially, the second guidewire 102 is advanced into the body of the patient. The first and second guidewires 101 and 102 are placed at different points and spaced apart to obtain an impedance measurement of a target tissue region. The target tissue region may be a portion of a tissue of a patient including but not limited to various organs, body lumens or cavities, such as various ducts or vessels, such as blood vessels comprising one or more occlusions. In one example, where the tissue region of interest is a portion of a blood vessel comprising an occlusion, the first guidewire 101 is advanced in an antegrade fashion to a proximal end of a vascular occlusion and the second guidewire 102 is advanced in a retrograde fashion to a distal end of the occlusion. The retrograde/antegrade approach is disclosed in the co-pending and commonly owned U.S. application Ser. Nos. 12/680,500 and 12/753,844, which are hereby incorporated herein by reference in their entirety.

The error correction electrode 103, which is configured as an ex vivo patch, is placed on the body of the patient such that the patch is in electrical communication with the body. The error correction electrode 103 is further connected to a measurement device 108. Thereafter, energy is delivered from the energy source 105, such as an RF generator, to the first and the second guidewires 101 and 102. In one example, the energy delivered to the tissue region may cause no significant tissue ablation to test the impedance of the tissue region. Alternatively, the energy delivered may be delivered at a level to cause tissue ablation. In another example, the energy delivered to test the impedance of the tissue region and the energy delivered to cause tissue ablation may be at different frequencies. The impedance measurement of the tissue region is then taken using measuring circuitry (not shown) in the measurement device 108, wherein the effect of capacitance caused by the first or the second guidewires 101 and 102 or by blood in the vessel is reduced, mitigated or corrected by the third terminal path created by the error correction electrode 103.

Figure 4:
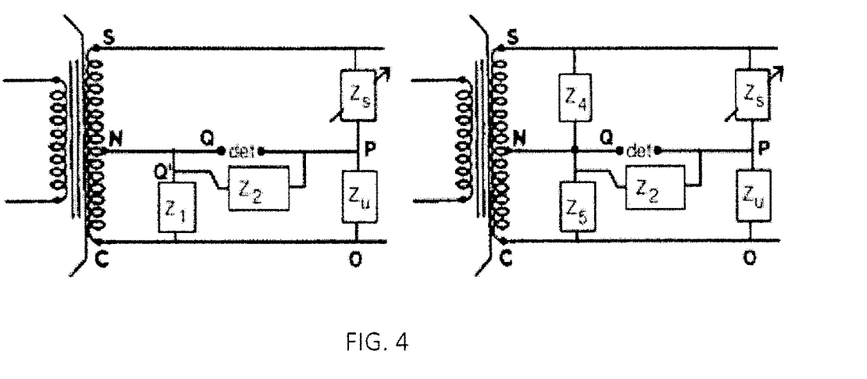
FIG. 4 is a circuit diagram of an example of an implementation of the apparatus for measuring in vivo tissue impedance.
Figure 5:
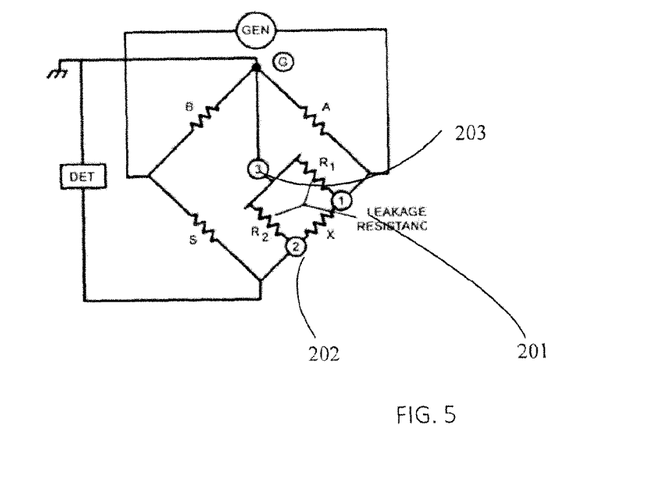
FIG. 5 is a partial block and partial circuit diagram of another example of an implementation of the apparatus for measuring in vivo tissue impedance.

Referring now to FIGS. 4 and 5, two examples of an impedance measurement using examples disclosed herein are shown. In FIG. 4, the shunt impedances are represented as $Z_1$ and $Z_2$, and the third-terminal N is connected to point Q. The bridge is driven by a signal presented at the primary side of the transformer, and is nulled by adjusting the value of known impedance Zs until the detector signal across Q-P goes to zero, and the value of unknown tissue impedance Zu is equal to the value of known impedance Zs. Transformer theory teaches that a single impedance $Z_1$ may be replaced by two identical impedances $Z_4$ and $Z_5$ which have a different value than $Z_1$, so that the left part of FIG. 4 is equivalent to the right part of FIG. 4, where $Z_4$ and $Z_5$ are equal and have no effect on the voltage at center-tap N. Thus $Z_1$ has no effect on the null point of the measurement. In addition $Z_2$ is connected across the detector and so may affect the magnitude of the detector signal away from the null point, but will not affect the null point itself.

Referring now to FIG. 5, the leakage resistances $R_1$ and $R_2$ are shunting the unknown tissue impedance X between guidewires 201 and 202. However, when the third terminal 203 is connected to a Wheatstone bridge and $R_1$ and $R_2$, the leakage resistance $R_2$ is across the detector and causes no error. In this example, the selection of insulation $R_1$ will have negligible effect.

Figure 6:
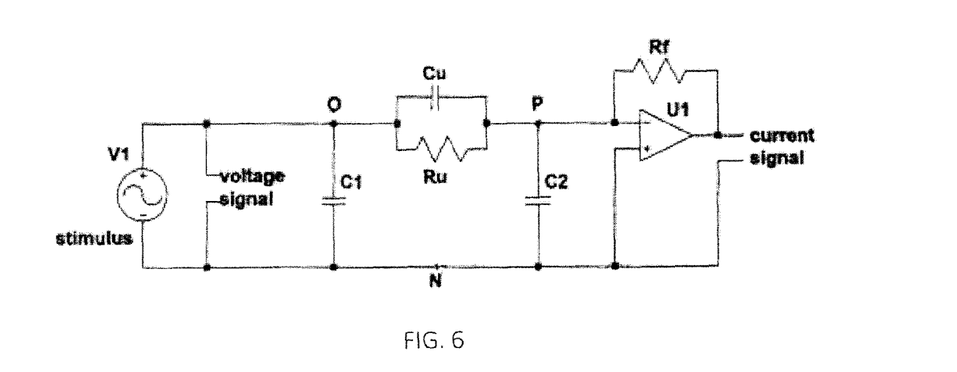
FIG. 6 is a circuit diagram of yet another example of an implementation of the apparatus for measuring in vivo tissue impedance.

Referring now to FIG. 6, where an example of an impedance measurement using examples disclosed herein is shown. In one example, an Agilent E4980A LCR meter by Agilent Technologies Inc.® (Santa Clara, Calif.) is used to measure the impedance of Cu and Ru in the presence of shunt capacitances C1 and C2 by dividing the driving stimulus "voltage signal" by the "current signal." The terminal connections to O, P, and third-terminal N are shown. C1 may have an effect on the voltage out of the stimulus source.

However, it does not matter because this measured voltage is used for the "voltage signal" in the impedance calculation only. Point P is a virtual ground maintained by amplifier U1 and its feedback resistor Rf, since there is no voltage from P to N then there is no current in C2, thus the value of C2 does not matter. Therefore, there is no need to "cancel" a capacitance with a precisely determined cancellation signal that other correction methods may have to employ, and in this case the value of C2 can change even during the measurement and it will have no effect on the calculated impedance of Cu and Ru.

It should be noted that examples described and shown in FIGS. 4-6 are illustrative only and it is contemplated that various other devices, modifications, and alterations may be utilized instead of or in conjunction with the various examples described above.

This technology also provides one or more kits for use in practicing the one or more methods described herein, where the kits typically include one or more guidewires and an error correction electrode. Kits may also include one or more delivery catheters, loading devices, connectors, or the like. In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other examples, the instructions are present as an electronic storage data file present on a suitable computer readable storage medium, e.g., CD-ROM, diskette, etc. In yet other examples, the actual instructions are not present in the kit, but means for obtaining the instructions from a remote source, e.g. via the Internet, are provided. An example of this is a kit that includes a web address where the instructions can be viewed and/or from which the instructions can be downloaded. As with the instructions, this means for obtaining the instructions is recorded on a suitable substrate.

EXAMPLE 1

Figure 7:
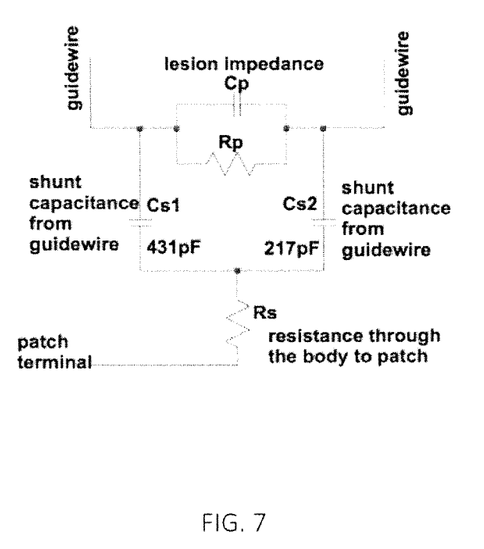
FIG. 7 is a circuit diagram of an example of one simulation of impedance testing characterizing an error of impedance measurement by using a patch to implement the third-terminal connection.

Referring now to FIG. 7, an example of simulation testing of one example of the impedance measurement method using known resistors and capacitors chosen to simulate the impedance of the physiological elements one may expect in a clinical setting while utilizing a third terminal path configured as a patch placed on a patient. In this example, the simulated target tissue capacitance Cp was simulated using a known capacitor (previously measured to be 10.17 pF) and the target tissue resistance Rp was simulated using a known resistor (previously measured to be 2156 ohms) Similarly, proper capacitors are chosen for shunting capacitance Cs1 and Cs2, respectively. With the third terminal path connected and when the leads of the shunting capacitors Cs1 and Cs2 are directly connected to the ground, shunting capacitances Cs1 and Cs2 are expected to have no effect of the accurate measurement of Cp and Rp as described in FIG. 6. The first goal of this testing is to verify the effectiveness of the disclosed method in obtaining accurate measurement of target tissue impedance Cp and Rp in the presence of the shunt capacitors Cs1 and Cs2. When the leads of the two shunting capacitors are connected to a resistor Rs that is used to mimic the resistance between the patch and the local tissue of the body, and then from the point connecting Rs to the ground, it is expected to introduce an error into the measurement of impedance, and the second goal of this testing is to quantify this error at various values of Rs including a range of 40 to 100 Ohms expected in clinical setting. All measurements are made using an Agilent E4980A LCR meter which provides the third terminal feature used in this testing. The results of this testing are summarized in Table 1.

TABLE 1

Simulated target tissue capacitance and target tissue resistance measurements

| | 100 kHz | | 250 kHz | | 500 kHz | | 1000 kHz | |
|---|---|---|---|---|---|---|---|---|
| Rs | Cp | Rp | Cp | Rp | Cp | Rp | Cp | Rp |
| 0 | 10.17 | 2156 | 10.17 | 2156 | 10.16 | 2157 | 10.16 | 2157 |
| 10 | 10.18 | 2158 | 10.21 | 2167 | 10.3 | 2201 | 10.54 | 2345 |
| 30.3 | 10.22 | 2161 | 10.4 | 2189 | 10.92 | 2294 | 12.75 | 2818 |
| 68.1 | 10.35 | 2168 | 11.08 | 2233 | 13.4 | 2488 | 21.4 | 4290 |
| 100 | 10.54 | 2174 | 12.03 | 2270 | 16.72 | 2670 | 32.01 | 6621 |

Rs: Ohms; Cp: pF; Rp: Ohms

Referring now to Table 1, where the measurements of the known impedance of Cp and Rp at various frequencies up to 1 MHz when the third terminal is connected in the presence of shunt capacitances Cs1 and Cs2 are shown. This bench testing also characterizes the error as a result of the existence of the resistor Rs that is used to mimic the resistance between the patch and the local tissue of the body, and the estimated value for Rs is in the range of 40 to 100 Ohms based on prior measurement for the resistance of the body when a third terminal configured as a patch electrode is used. As seen in Table 1, when Rs is not connected, the measurement result shows that the presence of the shunt capacitance Cs1 and Cs2 does not change the reported resistance or capacitance if the third terminal pathway is established. When Rs is connected, the error would be approximately 10% or less if a frequency of 250 KHz is used and thus can be considered as within margin of error, which suggests that it is valid to implement the simplified application of third-terminal correction method by using a patch on patient body surface if the ideal connection to the local tissue is not convenient. This testing further suggests that this approach is suitable for general clinical applications such as RF based ablations since the frequencies used in these applications are often in a similar range.

EXAMPLE 2

Referring now to Table 2, where a collection of data acquired in an animal study where one example of the impedance measurement method described herein was applied to measure the impedance of a tissue positioned inside a vessel at a given frequency.

TABLE 2

Animal study target tissue capacitance and resistance measurements (Capacitance: Cp; Resistance: Rp).

| | 1 | | 2 | | 3 | |
|---|---|---|---|---|---|---|
| | Cp | Rp | Cp | Rp | Cp | Rp |
| Without 3rd terminal | −9.9 | 2.6 | 56.3 | 1.81 | 15 | 2.97 |
| With 3rd terminal | 10.9 | 9.5 | 25.2 | 9.58 | 10.14 | 12.7 |

For each of the three data sets in Table 2, a new sample of the same type of tissue cut at exactly the same geometry was inserted into the vessel for measurement. Three measurements were made under different conditions according to the animal study protocol. Although the real true value of impedance for the three tissue samples is difficult to obtain since the impedance of the tissue type is subject to various conditions, from Table 2, it can be seen there is a difference between the measurements with and without the third-terminal connection. More specifically, measurement of Cp can change significantly in different conditions without the third terminal. As seen in the first measurement, Cp can be measured as a negative value which is impossible per prior knowledge; however, with the connection of the third terminal, the negative measurement can be corrected back to positive value. In addition, the third-terminal connection can also offset Rp back to the same baseline as well.

Accordingly, as illustrated and described herein this technology provides a number of advantages including providing methods and devices for measuring in vivo tissue impedance that reduce errors associated with shunt capacitance to provide for more accurate measurement of tissue impedance. In one aspect, this technology provides methods and devices for obtaining accurate measurement of target tissue impedance in vivo by using a third-terminal connection from a measuring device. This technology also improves the accuracy of in vivo impedance measurements of biological tissues, which may improve the accuracy of evaluations of the physiological condition of the tissue and proper implementation of medical treatment. Additionally, this technology is configured to reduce or eliminate errors affecting in vivo impedance measurements, which may improve treatment evaluation and improve the selection of treatment parameters and proper implementation of medical treatment.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for reducing in vivo shunt capacitance while measuring an impedance, the method comprising:
   advancing a first guidewire into a tissue region of a body of a patient, wherein the first guidewire comprises one or more electrodes electrically coupled to the tissue region;
   advancing a second guidewire into the body, wherein the second guidewire comprises one or more electrodes electrically coupled to the tissue region of the body of the patient and spaced from the first guidewire;
   electrically coupling an error correction electrode to the body of the patient, wherein the error correction electrode is structurally independent from the first guidewire and the second guidewire;
   applying a voltage across the first and the second guidewires; and
   measuring the impedance of the tissue region between the one or more electrodes of the first and the second guidewires while reducing an in vivo shunt capacitance using an electrical pathway created by the structurally independent error correction electrode when a voltage is applied between the first guidewire and the second guidewire.

2. The method as set forth in claim 1 wherein the error correction electrode is located on a third guidewire.

3. The method of claim 2 wherein the providing the error correction electrode in electrical communication with the body further comprises advancing the third guidewire into the body of the patient.

4. The method as set forth in claim 1 wherein the error correction electrode comprises a patch configured to be attached to the body of the patient.

5. The method as set forth in claim 1 wherein the advancing of the first guidewire comprises advancing in an antegrade fashion to a proximal end of a vascular occlusion and advancing of the second guidewire comprises advancing in a retrograde fashion to a distal end of the vascular occlusion.

6. The method as set forth in claim 1, wherein the shunt capacitance along a first length of the first guidewire and a second length of the second guidewire is reduced.

7. An apparatus for reducing in vivo shunt capacitance while measuring an impedance of a tissue region inside a body of a patient comprising:
   an energy source;
   a first guidewire and a second guidewire coupled to the energy source, the first and second guidewires configured to be advanced into a tissue region of a body of a patient, the first and second guidewires comprising one or more electrodes configured to be electrically coupled to the tissue region;
   an error correction electrode that is structurally independent from the first guidewire and the second guidewire and configured to be in electrical connection with the body of the patient; and
   a measurement device configured to measure the impedance of the tissue region between the one or more electrodes of the first and the second guidewires while reducing an in vivo shunt capacitance using an electrical pathway created by the structurally independent error correction electrode when a voltage is applied between the first guidewire and the second guidewire.

8. The apparatus as set forth in claim 7 wherein the error correction electrode is located on a third guidewire.

9. The apparatus as set forth in claim 8 wherein the third guidewire is configured to be advanced into the body of the patient.

10. The apparatus as set forth in claim 7 wherein the error correction electrode comprises a patch configured to be attached to the body of the patient.

11. The apparatus as set forth in claim 7 wherein the first guidewire is configured to be advanced in an antegrade fashion to a proximal end of a vascular occlusion and the second guidewire is configured to be advanced in a retrograde fashion to a distal end of the vascular occlusion.

12. The apparatus as set forth in claim 7, wherein the measurement device is configured to measure the impedance with a reduced shunt capacitance along a first length of the first guidewire and a second length of the second guidewire.

* * * * *